United States Patent
Wolfrum et al.

(10) Patent No.: US 11,278,013 B2
(45) Date of Patent: Mar. 22, 2022

(54) LARGE ANIMAL MODEL FOR DEVELOPING THERAPEUTIC AGENTS TO TREAT IMPAIRED OPHTHALMIC FUNCTION IN USHER SYNDROME

(71) Applicant: Usher 2020 Foundation, Atlanta, GA (US)

(72) Inventors: Uwe Wolfrum, Mainz (DE); Kerstin Nagel-Wolfrum, Mainz (DE); Nikolai Klymiuk, Hohenkammer (DE); Eckhard Wolf, Vierkirchen (DE)

(73) Assignee: Usher 2020 Foundation, Atlanta, GA (US)

( * ) Notice: Subject to any disclaimer, the term of this patent is extended or adjusted under 35 U.S.C. 154(b) by 0 days.

(21) Appl. No.: 16/859,860

(22) Filed: Apr. 27, 2020

(65) Prior Publication Data
US 2020/0337279 A1 Oct. 29, 2020

Related U.S. Application Data

(60) Provisional application No. 62/839,581, filed on Apr. 26, 2019.

(51) Int. Cl.
| | |
|---|---|
| *A01K 67/027* | (2006.01) |
| *C12N 9/22* | (2006.01) |
| *C12N 15/113* | (2010.01) |
| *C12N 15/86* | (2006.01) |
| *C12N 15/85* | (2006.01) |

(52) U.S. Cl.
CPC .......... *A01K 67/0276* (2013.01); *C12N 9/22* (2013.01); *C12N 15/113* (2013.01); *C12N 15/8509* (2013.01); *C12N 15/86* (2013.01); *A01K 2217/075* (2013.01); *A01K 2227/108* (2013.01); *A01K 2267/0306* (2013.01); *C12N 2310/20* (2017.05); *C12N 2750/14132* (2013.01)

(58) Field of Classification Search
CPC .......... A01K 67/0276; A01K 2217/075; A01K 2227/108; A01K 2267/0306; C12N 9/22; C12N 15/113; C12N 15/8509; C12N 15/86; C12N 2310/20; C12N 2750/14132
See application file for complete search history.

(56) References Cited

U.S. PATENT DOCUMENTS

| | | | |
|---|---|---|---|
| 575,846 | A | 1/1897 | Milo et al. |
| 7,126,039 | B2 | 10/2006 | Denning et al. |
| 10,729,112 | B2 | 8/2020 | Bolund et al. |
| 10,745,699 | B2 | 8/2020 | Van Wyk |
| 2018/0369414 | A1 | 12/2018 | Stankovic et al. |

OTHER PUBLICATIONS

Graham et al., Genome Biology, 16:260, 2014.*
Perelberg et al., Disease Models & Mechanisms (2018)11: 1-12.*
Gün et al., BioResearch Oepn Access, 3(6): 255-264, 2014.*
Sieren, J. of Clin. Investigation, 124(9): 4052-4066, 2014.*
Tian et al., Brain Research 1328: 57-70, 2010.*
G.J. Chader et al., Vision Research 42 (2002) 393-399.*
Klymiuk et al., Toxicologic Pathology, 2016, vol. 44(3) 346-357.*
PubMed, NCBI sequence NC_010444.4, Jan. 12, 2018.*
Goldmann et al., IOVS, 51(12): 6671-6680, 2010.*
Hauschild et al., PNAS, 108(29): 12013-12017, 2011.*
Never Lose Sight, First Edition Newsletter, Usher 2020 Foundation, Oct. 2015, 4 pages.
Usher Syndrome, Wikipedia, Online Available At: https://en.wikipedia.org/wiki/Usher_syndrome, Accessed from Internet on Mar. 29, 2019, 10 pages.
Usher Syndrome Research Advances, Foundation Fighting Blindness, Online Available At: https://www.blindness.org/usher-syndrome-research-advances, Jun. 2018, 4 pages.
Colella et al., Efficient Gene Delivery to the Cone-Enriched Pig Retina by Dual AAV Vectors, Gene Therapy, Short Communication, vol. 21, No. 4, Apr. 2014, pp. 450-456.
Goldmann et al., A Comparative Evaluation of NB30, NB54 and PTC124 in Translational Read-through Efficacy for Treatment of an USH1C Nonsense Mutation, European Molecular Biology Organization Molecular Medicine, vol. 4, No. 11, Nov. 2012, pp. 1186-1199.
Klymiuk et al., Tailored Pig Models for Preclinical Efficacy and Safety Testing of Targeted Therapies, Toxicological Pathology, vol. 44, No. 3, Apr. 2016, pp. 346-357.
Lentz et al., Deafness and Retinal Degeneration in a Novel USH1C Knock-In Mouse Model, Developmental Neurobiology, vol. 70, No. 4, Mar. 2010, pp. 253-267.
Mathur et al., Usher Syndrome: Hearing Loss, Retinal Degeneration and Associated Abnormalities, Biochimica et Biophysica Acta, vol. 1852, No. 3, Mar. 2015, pp. 406-420.
Poe, The Fall of the House of Usher (originally published Sep. 1839), 13 pages.
Williams et al., Gene Therapy Approaches for Prevention of Retinal Degeneration in Usher Syndrome, Gene Therapy, vol. 24, No. 2, Feb. 2017, pp. 68-71.

(Continued)

*Primary Examiner* — Thaian N. Ton (74) *Attorney, Agent, or Firm* — Kilpatrick Townsend & Stockton LLP (57) ABSTRACT

This disclosure provides new animal models for studying Usher syndrome and developing new therapy. The technology is implemented in pigs, and other large animals in which the ophthalmic architecture and function more closely resembles architecture and function of the human eye. The animals have a genetic modification in which all or a portion of a human gene known to cause Usher syndrome in human patients replaces the host gene. Animals can be cloned or bred to be homozygous at the targeted locus, whereupon they manifest symptoms and signs of Usher syndrome. Since a substantial portion of the targeted gene has been humanized, the animals can be used to develop and test pharmacological agents such as gene therapy that are sequence dependent.

16 Claims, 8 Drawing Sheets

Specification includes a Sequence Listing.

(56) References Cited

OTHER PUBLICATIONS

Tian et al., "Ush1c gene expression levels in the ear and eye suggest different roles for Ush1c in neurosensory organs in a new Ush1c knockout mouse," NIH Publilc Access, Published in final edited form as: Brain Res. Apr. 30, 2010; 1328: 57-70. doi:10.1016/j.brainres.2010.02.079.

Li et al., "Mechanistic Basis of Organization of the Harmonin/USH1C-Mediated Brush Border Microvilli Tip-Link Complex," Developmental Cell 36, 179-189, Jan. 25, 2016 [a]2016 Elsevier Inc. http://dx.doi.org/10.1016/j.devcel.2015.12.020.

Phillips et al., "Harmon in (Ush1 c) is required in zebrafish Muller glial cells for photoreceptor synaptic development and function," Dis Model Mech. Nov. 2011; 4(6): 786-800., Published online Jul. 14, 2011. doi: 10.1242/dmm.006429: 10.1242/dmm.006429.

Geleoc et al., "Disease mechanisms and gene therapy for Usher syndrome," Hearing Research journal homepage: www.elsevier.com/locate/heares, https://doi.org/10.1016/j.heares.2020.1079320378-5955/©2020 Elsevier B.V. All rights reserved, 12 pages.

Tohyam et al., "Age-Appropriateness of Porcine Models Used for Cell Transplantation," Cell Transplantation 2019, vol. 28(2) 224-228 [a] The Author(s) 2018, Article reuse guidelines: sagepub.com/journals-permissions DOI: 10.1177/0963689718817477 journals.sagepub.com/home/cll.

Toms et al., "Usher syndrome: clinical features, molecular genetics and advancing therapeutics," Ophthalmic Manifestations of Paediatric Systemic Diseases, Therapeutic Advances in Ophthalmology, 2020, vol. 12: 1-19, DOI: 10.1177/2515841420952194© The Author(s), 2020.

Böhm et al., "A gene therapy for inherited blindness using dCas9-VPR—mediated transcriptional activation," Sci. Adv. 2020; 6, eaba5614 Aug. 19, 2020, 10 pages.

Doetschman, "Influence of Genetic Background on Genetically Engineered Mouse Phenotypes," NIH Public Access, Published in final edited form as: Methods Mol Biol. 2009; 530: 423-433. doi:10.1007/978-1-59745-471-1_23.

Johnson et al., "Mouse models of USH1C and DFNB18: phenotypic and molecular analyses of two new spontaneous mutations of the Ush1c gene," NIH Public Access, Published in final edited form as: Hum Mol Genet Dec. 1, 2003; 12(23): 3075-3086. doi:10.1093/hmg/ddg332.

"Chromosomal position and activation of retroviral genomes inserted into the germ line of mice," Cell. May 1981;24 (2):519-29. doi: 10.1016/0092-8674(81)90343-3,1 page.

Saleski et al., "Optimized gene expression from bacterial chromosome by high-throughput integration and screening," bioRxiv preprint doi: https://doi.org/10.1101/2020.07.29.226290; this version posted Dec. 15, 2020, 41 pages.

Perleberg et al., "Genetically engineered pigs as models for human disease," 0 2018. Published by The Company of Biologists Ltd | Disease Models & Mechanisms (2018) 11, dmm030783. doi:10.1242/dmm.030783, 12 pages.

Ouyang et al., "Mutations in the alternatively spliced exons of USH1C cause non-syndromic recessive deafness," Original Investigation, Received: Mar. 11, 2002 / Accepted: Apr. 4, 2002 / Published online: Jun. 18, 2002, @Springer-Verlag 2002, Hum Genet (2002) 111 :26-30 DOI 10.1007/s00439-002-0736-0.

De Joya et al., "Usher Syndrome in the Inner Ear: Etiologies and Advances in Gene Therapy", Int. J. Mol. Sci., Apr. 10, 2021, pp. 1-15, vol. 22, Issue 8.

Toms et al., "Usher syndrome: clinical features, molecular genetics and advancing Therapeutics", Ther Adv Ophthalmol., Sep. 17, 2020, pp. 1-19, vol. 12, 3910.

Toualbi et al., "USH2A-retinopathy: From genetics to therapeutics", Experimental Eye Research, Dec. 2020, pp. 1-13, vol. 201, 108330.

Usher Foundation, "We have a path to clinical trials for those with Usher Syndrome", 2020, 4 pages. Excerpt from the Usher2020 Foundation website, downloaded Jul. 13, 2021.

Wolf et al., "Genetically modified pigs as donors of cells, tissues, and organs for xenotransplantation", Animal Frontiers, Jul. 2019, pp. 13-20, vol. 9, No. 3.

Yildirim et al., "SANS (USH1G) regulates pre-mRNA splicing by mediating the intra-nuclear transfer of tri-snRNP complexes", Nucleic Acids Research, Jun. 4, 2021, pp. 5845-5866, vol. 49, Issue No. 10.

Zettler et al., "A decade of experience with genetically tailored pig models for diabetes and metabolic research", Anim Reprod., 2020, pp. 1-14, 17(3).

\* cited by examiner

FIG. 1A

FIG. 1B aggcaagggggttctgccaggtggaaaccagaaatctgcattctgtaccccctgttcaggcca
gaaacctcaagggctgggcccagcatggcctctttgtgttaggccaggcagacttcctgaacc
ctgaagatatccagagaaagaggcaaagatgctccagctctcctctgaggaccaatcaggtgg
gagcttgcagcttccagcagcagcttctccctgtgcagcctgaggccctggaccatgttgttg
gccctggatgctggaggacagagggacccaaggacccctcaagcctccaccctgccctcttac
tcagtctgggctgaagagcgagctaaggatgtagtacataaagattcatactgagctgtccca
gggagtgaaattcggggctcttgacccaccagctctcctgggactgaggtgctaatgaaacag
ctcttgaccctgaccttggactcctggccattgacgtcagcaaaattgaaataatgtaacctg
actctcccctggggtggaaggggagctctacagggacctggggaggggaaggagtggccaga
ggggccaacccagcttagaccaggacaggacaaggaagaattcagtggcaaggttcttcgggc
ggatgggatgtgctatctgagcgagtggcctaaatcttttctgaaagcggttatccggcacta
cagccaccatcaggtaagacaatgggcttctgccgacacgggtggtgccaccctggacacagg
tgacataaccatggaggtgatcagcagcacggctgccgtggggtgcatcactgtcacacagg
ggttcacaggtatgatatgcatatgcatccctgtgtgcccctgcatcaccccacctggggtca
ggctgatgactacatccgaaagcacaaggtgctcctgtggccacactggcatggtcggcgca
gtctcatgttggaaccagagggccagcctggcctctggcttccctcctcttctcacaaccatg
aggagacgctggggaggttccccccacccccacagtggcctcccccttcctgctgctactggg
ggtgctgggcctggagctgtaattctgcccttgggttttccagGTGGATTTCCTGATTGAAAA
TGATGCAGAAAAGGATTATCTCTACGATGTGCTG<u>CGG</u>ATGTACCACCAgtaagtgtgctgggt
cccactcctgtggaccaccccgggtacctctgtcctcagggagccctggggtgtgttgttctg
agacaggaggacctcccactcccatcctgggaagctcagggaggcagatgcctgggaatcaaa
tggacacgcctttcactggtttcaacaaatatttacacagaggtgctgtgcgtggctctgtgc
taggggctaggagtacgcctgtcagcaagacagatgagttgctgccctcaagttgctcatggt
ctgatgggggaggctgtcagatagtccgagaggttcaacaaagtttgatgtctgggataggac
cggaaatgccagctggccttagcacca

FIG. 1C agggaaggaggtactgtcagatctaggccagaaatctgcattctgtaccccctgctcaggcca
gaaatcccaagggctgggcccagcatgtccctctgtggtgggacggacagactgccccggtc
ttccagaaccttgggatacccacagaaagaggtaacgctgctctggccctcttctgaggacg
agtcagtggagagcatgcagcttccagctgcagcctctctatgaagggctgaggccctgggcc
gggaggctggaggagagagggacccagtgacccccaagcttccaccttgctctgttacccgt
tcttgggctgaagagagacccaaaaatacagtgtagagattcacactgaggtaactcagggag
tggaattcagggcctcccactgggattgaggtgctaatgacacaactcctgaacctgaccta
gagtgccagccattgacgtcaacaaagttgaaatgatgtaacctgacgctcccctgcggggc
ttgtgcaggggcctggggaggggaaggagtggccatgaaactgactagtggacagaacccag
ctaaggtcaggacaagacagagtgaaggtcccctggcactgatgttacagaagaattcggtgg
taaggggcttctggagagtggcatgtgctatctaagcgagtggcccaaatccttcctgaaagc
atttatccggcactacagccaccatcaggtaagacagtgggcttcttctggccatggatgaca
cagccatggggtgagcagcagcactgccatggcagcgtgtcactgtcacatggggattcaca
tatgtacctatgtgtgttcatccccgtgtgtgcacatattgccccacctggggacgaagggtg
cctggccacatctggaggggcagcggtactcctgtggccacgttggggtggtctgcataggtc
tgatgcattggggtcagaggggcagcctggcctgtggctcctcttctctcctcaactccag
ccctgaaaagctgctggggaggcccttggggatgacctctcctccctgaggtctgctatgggt
gggggtgctgagcctggagctgtgattctgctattggattttccagGTGGATTTTCTGATTGA
AAATGATGCAGAGAAGGACTATCTCTATGATGTGCTG<u>TGA</u>ATGTACCACCAgtaagtgtgctg
ggtccagctcttgtgggccacttgggttcctttgtcttcagggagccctgggatgggttgttc
tgagacagaggagctcagagggtggatgctcacggctcctggaaatcaaatggacataccatt
cactcatttcagcaactatttacacaagtactttgtacttggctttgtactaggggctgggta
tagttgtgagccagacagattggtctctgttttcaggttgctcacagtctgatggaggaggct
gtctagtagccagatagattctatagagcatgattgttgggacagaacaagaaatgccagctg
gccacagcccctt

LARGE ANIMAL MODEL FOR DEVELOPING THERAPEUTIC AGENTS TO TREAT IMPAIRED OPHTHALMIC FUNCTION IN USHER SYNDROME

REFERENCE TO RELATED APPLICATIONS

This application claims the priority benefit of provisional application 62/839,581, filed Apr. 26, 2019, having the same title. The priority application is hereby incorporated herein in its entirety for all purposes.

FIELD OF THE INVENTION

The technology disclosed and claimed below relates generally to the fields of genetic engineering, animal cloning, signs and symptoms of Usher syndrome, and ophthalmic medicine. This disclosure includes a genetically modified pig containing at least one mutation evocative of Usher symptomatology that that exemplifies an improved animal model screening therapeutic agents and treatment protocols.

BACKGROUND

Every day, people all over the world are slowly losing their sight due to the genetic disorder known as Usher syndrome. The real tragedy is that these people have already lost their hearing, and struggle to maintain their balance (Usher 2020 Foundation). In spite of these challenges, people with Usher syndrome are fully capable, both intellectually and emotionally. Less than 25% of young people with Usher syndrome show evidence of mental or behavioral impairment. It is estimated that Usher syndrome affects between 25,000 and 40,000 people in the United States, and as many as 400,000 around the world.

Hearing impairment in USH is caused by abnormal development of hair cells in the inner ear. Children with Usher syndrome are usually born with moderate to profound hearing loss, caused by retinitis pigmentosa (RP). It manifests initially as night-blindness and a loss of peripheral vision because of progressive degeneration of cells in the retina. As RP progresses, the field of vision narrows until only tunnel vision remains. Macular holes and cataracts may also occur, leading to an early decline in central vision.

Usher syndrome is inherited as an autosomal recessive disorder. It has a heterogeneous presentation, because it is a consequence of mutations to any one of at least 12 different genes (Wolfrum 2011; Mathur and Yang 2015; Wolfrum et al. 2018). There are three types (USH1, USH2, and USH3), and other less typical forms. USH1 is the most severe type, characterized by profound hearing loss starting at birth, vestibular areflexia, and pre-pubertal onset of vison loss.

Currently there is no cure for Usher syndrome in any of its forms. Treatment is generally limited to the management of hearing, vision, and balance problems. Early diagnosis helps the managing clinician tailor educational programs to the severity of hearing and vision loss and a child's age and ability. Treatment may include the use of hearing aids, assistive listening devices, and cochlear implants. Unfortunately, retinal degeneration in USH1 is an irreversible process, resulting in impaired vision starting in childhood, which leads to complete blindness by the third decade of life.

SUMMARY

This disclosure provides new animal models for studying Usher syndrome and developing new therapy. The technology is suitable for use in large animals, in which the ophthalmic architecture and function more closely resembles architecture and function of the human eye. The animals have a genetic modification in which all or a portion of a human gene known to cause Usher syndrome in human patients replaces the endogenous homolog. Animals can be cloned or bred to be homozygous at the targeted locus, whereupon they manifest symptoms and signs of Usher syndrome. Since part or all of the targeted gene has been humanized, the animals can be used to develop and test pharmacological agents that are sequence dependent, such as gene therapy.

Various aspects and embodiments of the invention are described in the sections that follow, the accompanying drawings, and the appended claims.

DRAWINGS

FIG. 1B shows the vector sequence containing the porcine USH1C fragment that was replaced (SEQ. ID NO:1). The exon is shown in capital letters. The underlined codon is the porcine R31 codon, corresponding to the R31X codon in humans.

FIGS. 5A and 5B show results of visual acuity testing. Five USH pigs and 5 wild-type littermate controls were tested for their ability to cross a parcours containing obstacles under normal light conditions and in darkness. The time for passing the track and number of snout touchings in representative experiments are shown (mean±standard deviation).

FIGS. 6A to 6E show results of physiological and morphological characterization of pigs modeling Usher syndrome in humans (USH). FIG. 6A: the USH1C pigs were almost entirely deaf.

DETAILED DESCRIPTION

While hearing impairments in USH can be compensated with hearing aids and cochlear implants, there is no practical therapy for USH in the eye.

This disclosure provides a new technology that includes animal models with more features of Usher syndrome in humans—with the phenotypic characteristics and underlying pathophysiology of ophthalmic impairment. It establishes a new basis for developing ophthalmic medicines and other agents for treatment of Usher syndrome.

Inadequacy of Mouse Models for Usher Syndrome

In the eye and in the ear, proteins expressed by the USH gene mutations are primarily located in the mechano-sensitive hair cells and the rod and cone photoreceptor cells, respectively. In the hair cells, the USH protein networks are essential for the correct differentiation of the hair bundles as well as for the function of the mechano-electrical transduction complex in the matured cell. In the photoreceptor cells, USH proteins are located in the ciliary region and participate in intracellular transport processes. In addition, a USH protein network is present in the so-called calyceal processes.

USH has been modeled in mouse strains. Two research groups have been working with mouse models for USH type 1B, caused by mutations in the myosin VIIa (MYO7A) gene to test lentiviral vector gene therapy (Hashimoto et al., Zallocchi et al.). In the second study, the vector protected the photoreceptors of the transgenic mouse from acute and chronic intensity light damage, indicated by a significant reduction in photoreceptor cell loss, and restoration of the α-transducin translocation threshold in the photoreceptors. There are also models for USH in zebrafish (Blanco-Sanchez B et al.) and rats (Held N. et al).

In our opinion, the lack of calyceal processes and the absence of a prominent visual phenotype in the mouse disqualifies mice as models for studies on the ophthalmic component of USH.

Advantages of These Animal Models for Developing New Therapy for Usher Syndrome

To address the lack of adequate animal models for USH, we developed a new technology to create genetically modified animals that more fully represent signs and symptoms of USH, including but not limited to ophthalmic impairment.

Animals bearing one or more gene alterations that are prepared in accordance to this disclosure provide a superior means by which to develop and test new therapeutic agents and strategies for the treatment of USH. The advantages include the following Ocular anatomy and the structure of photoreceptor cells in large animals such as the pig more closely resemble humans than previous animal models;

The models described here replicate characteristics of USH—not just in terms of ocular impairment, but also the retinal changes and ophthalmic impairment that presage vision loss;

The animals can be used to test therapeutic agents and strategies for both ocular and ophthalmic features of the condition;

A substantial part of the animal's endogenous gene may be substituted with the corresponding portion of a gene from a human patient with USH. This results in the causative mutation being placed in the context of a human gene sequence. The animals can be used to test therapeutic approaches that are sequence dependent, such as gene editing.

Gene Modifications and Terms Used

In accordance with this disclosure, genetically modified non-human animals can be obtained that have one or more mutations in one or more genes or encoding regions that underlie the signs and symptoms of USH. Exemplary are those put forth in Table 1, including but not limited to the USH1c gene, which encodes harmonin protein, a PDZ domain-containing protein expressed in the inner ear sensory hair cells.

Genetically modified animals in accordance with this disclosure are vertebrates, typically mammals, and preferably large animals having ocular features and markers that resemble those of humans. Exemplary are pigs, sheep, and other mammals of at least 6 pounds when fully grown, suitable for animal cloning by way of somatic cell transfer. In places where the this disclosure refers to pigs, it is understood that the technology can be applied to other species, mutatis mutandis. Conversely, where the technology of this invention refers to animals without specifying or otherwise requiring a particular species, it is implied that pigs, sheep, and other clonable large animals are exemplary.

All or part of an expressible USH gene (such as a USH1c gene) that is normally endogenous to the genome of an animal has been substituted in the genetically modified animal with an exogenous nucleic acid, wherein the presence of the exogenous nucleic acid in the genome of the genetically modified animal prevents expression of a functional USH gene product from the USH gene, as constituted after genetic modification. For example, all or part of the endogenous gene (for example, an exon, with or without flanking and/or internal non-encoding regions) is replaced with the corresponding potion of the corresponding, including a mutation that is thought to cause Usher syndrome when homozygous in humans. Alternatively, the gene may be caused to have a point mutation, which adds, deletes, or changes one or more codons.

Following the genetic modification, the species homolog of the gene referred to has been modified so as to encode a gene product having a changed amino acid sequence or a shorter amino acid sequence, whereby the gene product no longer performs its normal physiological function, or wherein the gene is modified to be non-transcribable or non-translatable. Any of these changes will prevent or inhibit expression of a functional USH1c gene product from the USH1c gene in the genetically modified animal. Included are changes to non-encoding regions of the genome that alter expression of the gene such that it is expressed in the wrong tissue, or in insufficient quantities or at inappropriate times in tissues affected in Usher syndrome.

Any change to the endogenous gene referred to that has the desired effect on transcription nor protein function is included. In one illustration of the invention, the exogenous nucleic acid contains a nonsense mutation or a stop codon that terminates transcription of protein encoded by the USH1c gene. Other possible mutations of the USH1c gene that correspond to known human genotypes of Usher syndrome are shown in Table 2. Exemplary is a change in the encoding sequence of the gene that causes the gene product to include the R31X mutation that is known to cause Usher syndrome when homozygous in humans. Preferably, any exogenous nucleic acid or transgene introduced into the genome of the genetically modified animal does not contain an exogenous drug resistance gene. Such a gene may have been present in a parental cell for facilitating introduction of a transgene, but if so, it has been removed, possibly leaving a lox recombination site.

Unless explicitly specified or required, any of the genetic modifications referred to above and in this disclosure may be present in the genetically modified animal either homozygously or heterozygously, either in parental cells used for cloning, in the genetically modified animal, or in tissue or cells obtained therefrom. In homozygous form, the animal will probably but not necessarily have one or more phenotypic features of Usher syndrome as put forth in this disclosure, either intracellularly, in tissue architecture, or in ocular, vestibular, or ophthalmic function. For example, intracellular architecture of photoreceptor cells in an eye of the animal is detectably abnormal when analyzed by transmission electron microscopy (TEM) as a result of the presence of the exogenous nucleic acid in the genome of the animal In heterozygous form, the animal will typically be phenotypically silent, but can serve as a control animal for a familial homozygous animal, or as a breeding source for obtaining homozygous animals having the syndrome.

Usher Syndrome Phenotypes and Genes

Usher syndrome is inherited as an autosomal recessive condition. Several genes have been implicated or associated with Usher syndrome using linkage analysis of patient families and DNA sequencing of the identified loci (Table 1). A mutation in any one of these genes that substantially interferes with gene expression or protein function is likely to result in Usher syndrome.

Usher syndrome I

Subjects with Usher I are born profoundly deaf and begin to lose their vision in the first decade of life. They also exhibit balance difficulties and learn to walk slowly as children, due to problems in their vestibular system.

Usher syndrome type I can be caused by mutations in any one of several different genes: CDH23, MYO7A, PCDH15, USH1C or USH1G. These genes function in the development and maintenance of inner ear structures such as hair cells (stereocilia), which transmit sound and motion signals to the brain. Alterations in these genes can cause an inability to maintain balance (vestibular dysfunction) and hearing loss. The genes also play a role in the development and stability of the retina by influencing the structure and function of both the rod photoreceptor cells and retinal pigmented epithelial (RPE) cells.

Usher syndrome II

Subjects with Usher II are generally hard-of-hearing rather than deaf, and their hearing does not degrade over time. They do not seem to have noticeable problems with balance. They typically begin to lose their vision in the second decade of life, and may preserve some vision even into middle age.

Usher syndrome type II may be caused by mutations in any of three different genes: USH2A, GPR98 and DFNB31. The protein encoded by the USH2A gene, usherin, is located in the supportive tissue in the inner ear and retina. Usherin is critical for the proper development and maintenance of these structures, which may help explain its role in hearing and vision loss.

Usher syndrome III

Subjects with Usher syndrome experience a progressive loss of hearing, and roughly half have balance difficulties. Currently, mutations in only one gene, CLRN1, have been linked to Usher syndrome type III. CLRN1 encodes clarin-1, a protein important for the development and maintenance of the inner ear and retina. Its role in hearing and vision loss needs further investigation.

This section has been adapted from the Wikipedia entry on Usher Syndrome, accessed on Apr. 22, 2019. For further information, the reader is referred to Petit, C (2001): "Usher syndrome: from genetics to pathogenesis," Annual Review of Genomics and Human Genetics. 2: 271-97; and Reiners, J; Nagel-Wolfrum, K; Jurgens, K; Marker, T; Wolfrum, U (2006): "Molecular basis of human Usher syndrome: deciphering the meshes of the Usher protein network provides insights into the pathomechanisms of the Usher disease," Experimental Eye Research. 83 (1): 97-119.

Incorporation of Usher Syndrome Mutations into the Genome of a Non-Human Animal

Any means of introducing the desired mutation into the germline to produce the desired genetically modified animal can be used. Animal cloning, or somatic cell nuclear transfer (SCNT) can be performed according to standard methods, as described in GB 2318578 and GB 2331751 (Roslin Institute). A nuclear donor cell is inserted into a suitable recipient cell, such as an enucleated oocyte. Alternatively, to the extent that is technically feasible, a genetically modified parental donor cell can be epigenetically reprogrammed into a viable zygote. EP 2121902; Chung, Lanza et al. (2009), Cloning and Stem Cells 11(2).

Before the nuclear transfer or reprogramming, the genetically modified parental cell is produced using a suitable genetic engineering vector. For example, insertion of transgenes can be accomplished using a bacterial artificial chromosome (BAC) or a P1-derived artificial chromosome (PAC). The vector containing the transgene to be inserted is introduced into the parental cell, whereupon insertion into the host genome is promoted: for example, by homologous recombination, or using a gene editing tool, such as the bacterial CRISPR/Cas9 system or a transcription activator-like effector nucleases (TALEN). As illustrated below, the parental cell may be co transfected with the BAC vector together with plasmids encoding gRNA and Cas9.

Clones containing the appropriately modified gene are then identified and retrieved. By including a drug resistance gene in the vector (a means for clonal selection, such as a neomycin resistant gene), genetically modified cells can be selected, and then genotyped. In this case, the drug resistant gene is preferably placed in the gene vector with a means for removing it later: such as a loxP site on either side. Once parental cells with the appropriate modification of the USH gene is identified and selected, the drug resistance gene is removed (for example, using a Cre recombinase vector). Genotyping to identify properly modified genes can be performed, for example, by qPCR-based loss-of-wild-type-allele (LOWA) analysis.

After nuclear transfer or reprogramming, the zygote containing the genetic modification is implanted into a suitably prepared surrogate. Offspring are genotyped and phenotyped to identify animals of interest, for example to study features of Usher syndrome or its treatment.

Use of the Animals and Tissue for Developing New Therapy for Usher Syndrome

Genetically modified animals according to this disclosure can be used, for example, for testing a pharmaceutical agent or composition for efficacy in the treatment of Usher syndrome. The small molecule drug, biological, gene therapy agent, or other therapeutic composition or treatment is administered either systemically or in and around the eye of the genetically modified animal. Then the user determines whether the administering of the agent or composition improves intracellular architecture and/or function of retinal cells in the eye of the animal.

By way of illustration, the agent may be an adeno-associated virus (AAV) or other vector that contains gene encoding a functional USH gene product when expressed in cells located in or around the eye, or configured for translational read-through (TR) therapy of the genetically modified USH gene, or for genetic repair of the genetically modified USH gene. The animals may also be used to test cellular therapy with fully functional retinal cells prepared for that purpose.

Included as part of this disclosure are tissues and cell populations that has been removed or isolated from a genetically modified animal as heretofore described. The tissue or cell population will have substantially the same genome in which all or part of an expressible USH gene that is normally endogenous to the genome of the animal has been substituted in the genetically modified pig with an exogenous nucleic acid to prevent expression of a functional USH gene: optionally, with flanking and/or internal non-coding regions. Such tissues or cell populations can be used to study intracellular and intercellular manifestations underlying Usher syndrome, in comparison with matched cells not having the genetic modification. Therapeutic agents (such as small molecules, biologicals, and gene therapy vectors) can be tested at the cellular level by adding the agent to the tissue or cell population in culture, and determining whether there is a change in markers or function of the sample as a result of the presence of the agent.

Exemplary Pig Model for USH1

We generated a transgenic USH1 pig model by targeting the USH1C gene on Chr2:42Mb in the porcine genome. To do this, we replaced the porcine exon 2 and the flanking intronic sequences of USH1C with the corresponding portion of a human gene bearing the R31X mutation that is often the cause of USH1. This mutation introduces a premature stop-codon into USH1C exon 2, which either prevents expression of the gene, or expresses on a very short non-functional harmonin protein.

Figure 1A:
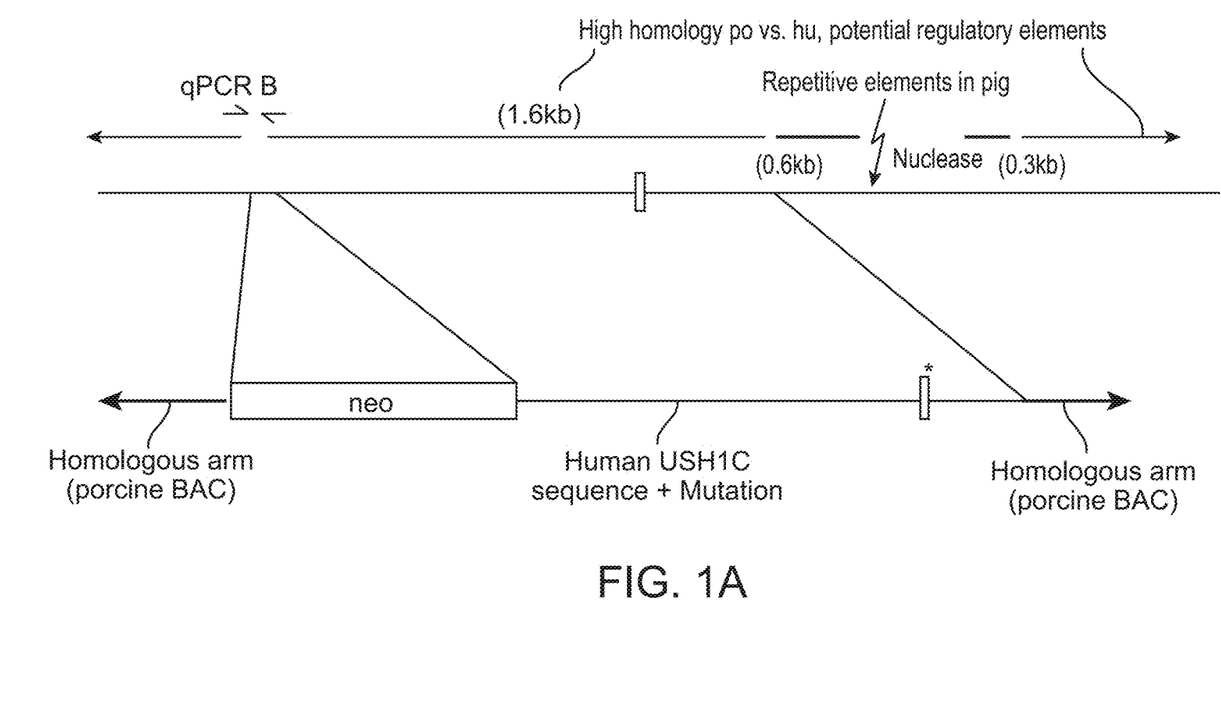
FIG. 1A is a genetic map showing targeting strategy to generate a genetically modified pig that illustrates aspects of this invention. Exon 2 of the porcine USH1C gene was targeted for replacement with the sequence of the corresponding portion of the USH1C gene of a human patient with Usher syndrome (USH), bearing an R31X mutation.

FIG. 1 is a genetic map showing the targeting strategy of the USH1C exon 2. We replaced the porcine exon 2 plus up- and downstream intronic regions (second line) by the human ortholog (third line), containing the R31X mutation (asterisk). To avoid unwanted consequences of the modification, potentially regulatory function were entirely replaced: specifically, a 1.6 kb element of high homology between human and pig. A selection cassette for neomycin resistance (neo), flanked by loxP sites was located upstream of the human fragment. A gRNA sequence positioned downstream of targeting region was used to promote homologous recombination by introducing a double strand break.

The intended modification was engineered into a bacterial artificial chromosome (BAC) according to the general methodology provided in Klymiuk et al. 2013 and Klymiuk et al. 2012, infra.

Figure 1C:
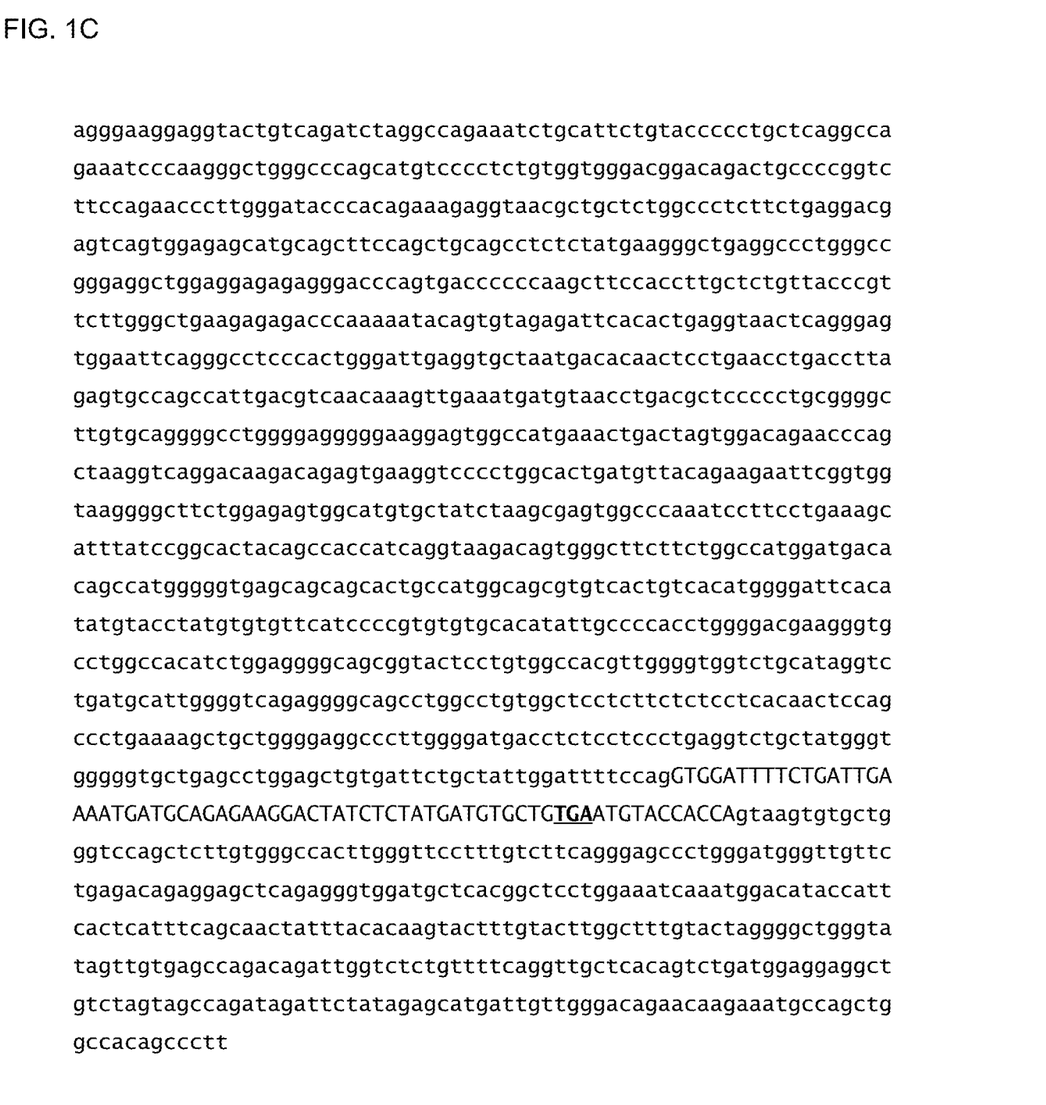
FIG. 1C shows the vector sequence containing the human USH1C fragment (SEQ. ID NO:2) that was inserted in place of the porcine fragment. Exon 2 is shown in capital letters. The underlined codon carries the disease carrying mutation R31X.

FIG. 1B shows the vector sequence containing the porcine USH1C fragment that was replaced (SEQ. ID NO:1). Total length: 1539 base pairs, the exon shown in capital letters. The underlined codon is the porcine R31 codon, corresponding to the R31X codon in humans. FIG. 1C shows the vector sequence containing the human USH1C fragment (SEQ. ID NO:2) that was inserted in place of the porcine fragment. Total length: 1524 base pairs, Exon 2 shown in capital letters. The underlined codon is the disease carrying mutation R31X.

Figure 2A:
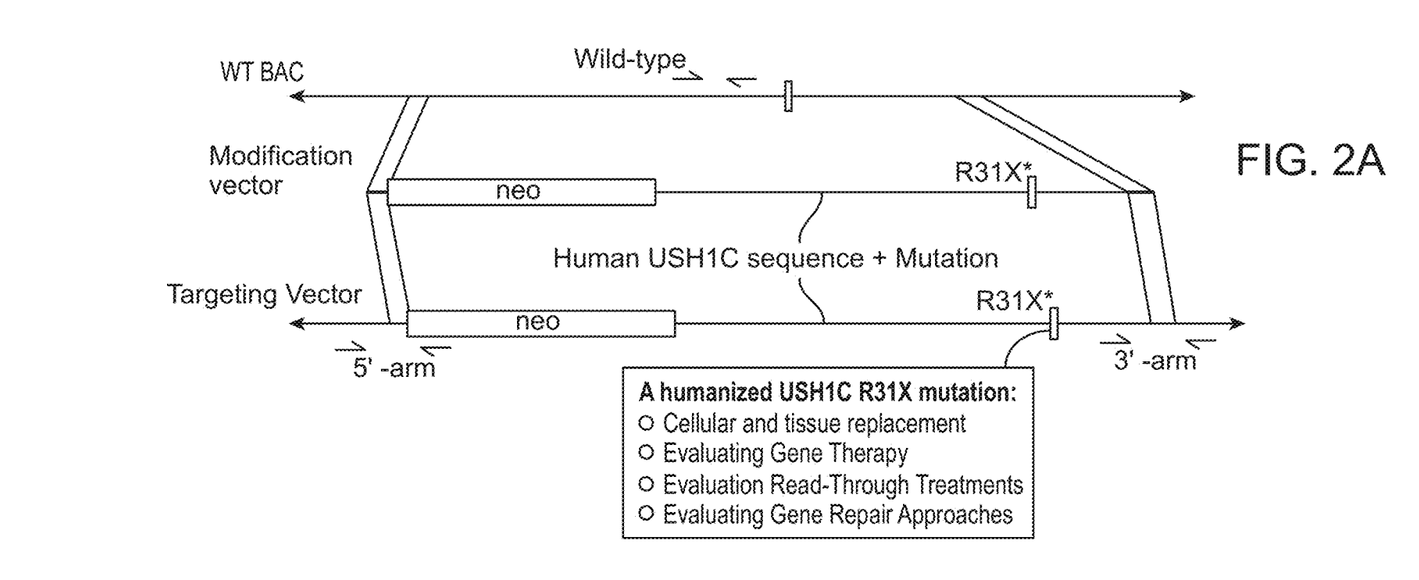
FIG. 2A is a genetic map showing the preparation of a bacterial artificial chromosome (BAC) vectors used for modifying nuclear donor cells.
Figure 2B:
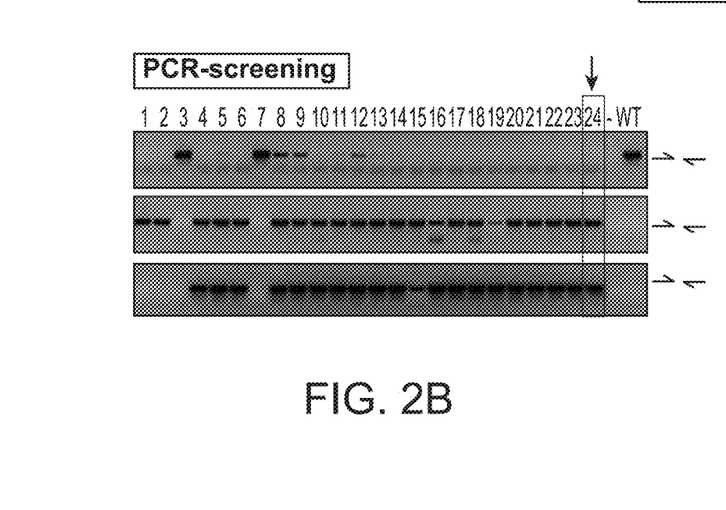
FIGS. 2B and 2C show results of end-point PCR and high-resolution restriction enzyme digest analysis, respectively, confirming proper construction of the BAC clones.
Figure 2C:
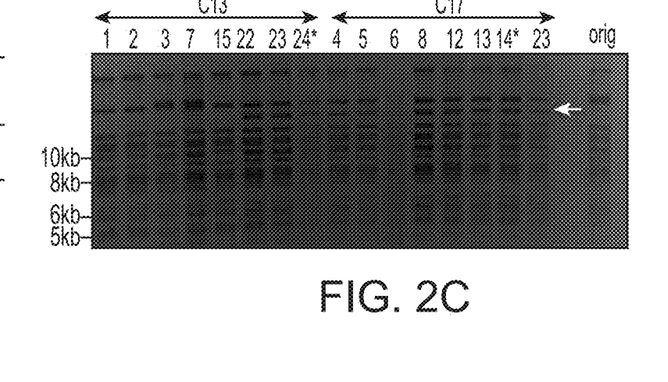

FIG. 2A is a genetic map showing how the BAC targeting vector was generated. CH242-515C3 on chromosome 2 was identified as carrying the USH1C locus in the porcine gene. It was modified by bacterial recombineering. FIG. 2B shows the results of end-point PCR (lower left), confirming the proper arrangement in the resulting clones. FIG. 2C shows results of high-resolution restriction enzyme digest. The consistent band pattern indicated that the integrity of the BAC was maintained whereas the occurrence of a single 15 kb band indicated the site-specific introduction of the desired modification (white arrow).

Figure 3A:
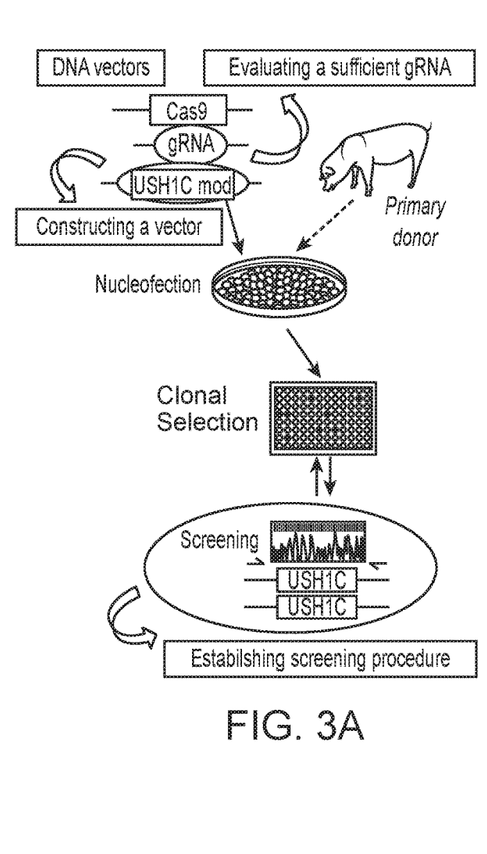
FIG. 3A illustrates the targeting strategy and screening of pig primary cells.

FIG. 3A is an illustration that shows the strategy for targeting and screening of pig nuclear donor cells. The modified BAC was co-transfected with CRISPR encoding gRNA and Cas9 plasmids into male and female cells. Single cell clones were generated and selected using neomycin.

Figure 3B:
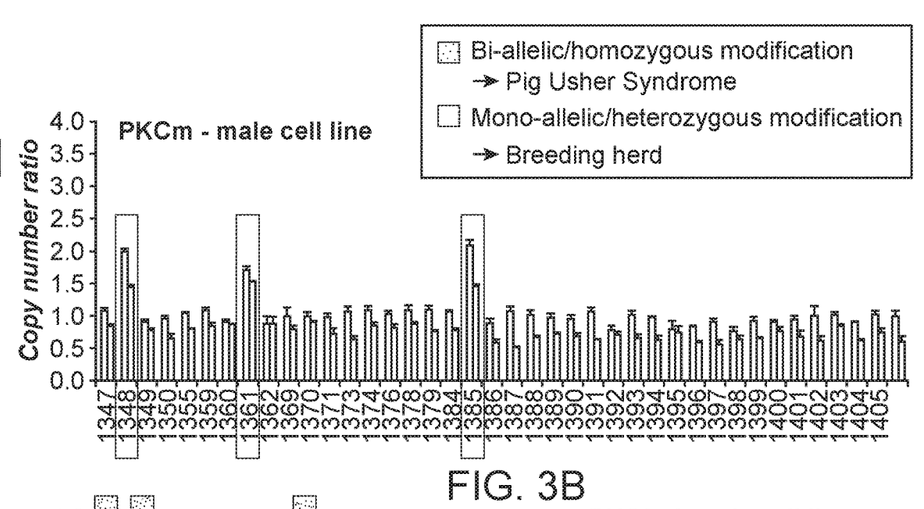
FIGS. 3B and 3C show results of screening of nuclear donor cells for the appropriate mutations by qPCR-based loss-of-wild-type-allele (LOWA) analysis.
Figure 3C:
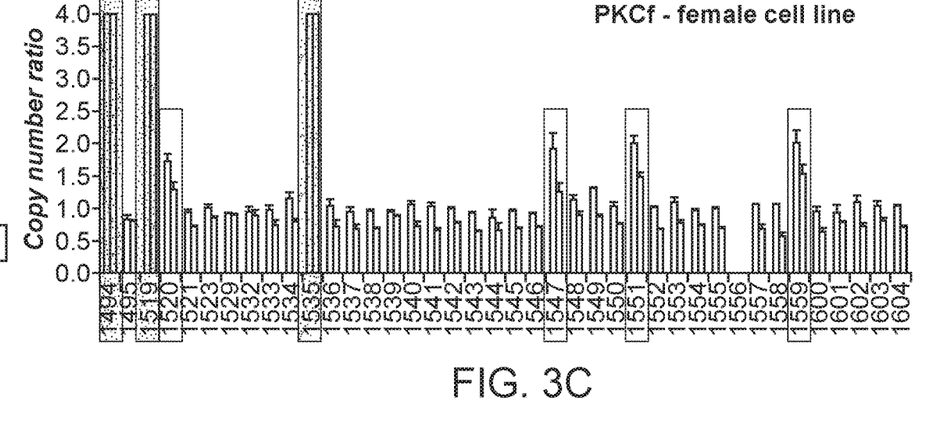

FIGS. 3B and 3C shows results of screening of the clones for the presence of the intended mutations by wild-type-allele (LOWA) analysis. In male cells we obtained three heterozygously targeted clones (FIG. 3B). In female cells we obtained four clones with heterozygous targeting and three with homozygous targeting (FIG. 3C).

Homozygously modified female cells were used to create USH1C$^{R31X/R31X}$ pigs by somatic cell nuclear transfer (SCNT). First, the nucleus donor cells were treated to remove the neomycin selection gene. Cre-encoding mRNA was introduced into the cells by lipofection, which excised the neomycin selection cassette via Cre-lox mediated recombination. The nuclei of these donor cells were transferred into enucleated oocytes, and the resulting clones were implanted into surrogates. In two litters, we obtained 5 and 9 genetically modified offspring, respectively.

Figure 4:
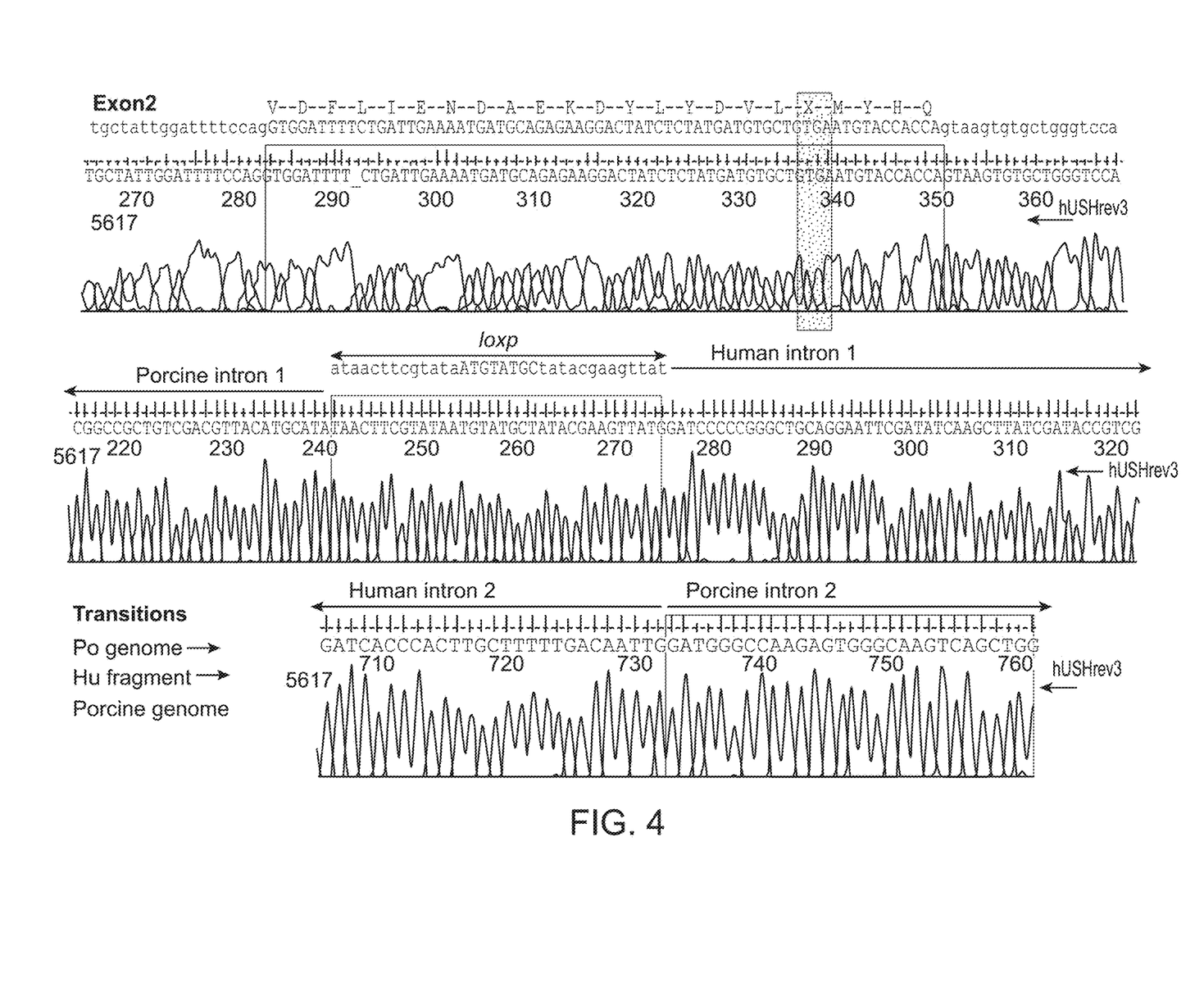
FIG. 4 shows results of Sanger sequencing to confirm presence of a modified USH1C gene and removal of the neomycin resistance gene in pigs produced by somatic cell nuclear transfer.

FIG. 4 shows results of Sanger sequencing of genomic DNA from the piglets produced from the SCNT, to determine whether there was modification of the USH1C gene. The region around exon 2 and the transitions from the porcine genome into the modified region were amplified and sequenced in animal 5617. Exon 2 clearly comprised the human sequence, including the TGA codon responsible for the R31X mutation (upper panel, blue box). The selection cassette has been sufficiently removed, indicated by the transition of pig genomic sequence to the remaining single loxP site and the adjacent human intronic sequence (middle panel). Accordingly, the transition of downstream end of the modification to the pig genomic sequence was confirmed as well.

All animals carried the human exon 2 including the codon for the R31X mutation. Of five surviving animals, three retained the selection cassette, whereas two of them have sufficiently removed it from both alleles.

Phenotype Analysis of Pigs Bearing the R31X Mutation

We determined the phenotype of the exemplary USH1C pig model at two time points: three weeks and 12 months of age. Transgenic USH1C$^{R31X/R31X}$ piglets of each age were analyzed in comparison to age-matched wild type pigs for physiological function of hearing and vision in vivo. We also did comprehensive molecular and histological analysis of the cochlear and the retina after scarification in vitro. In parallel, we continually monitored the behavior of the USH1C$^{R31X/R31X}$ pigs, and performed behavior tests to determine their visual orientation.

Behavior analysis. Already at birth, the USH1C$^{R31X/R31X}$ pigs showed pronounced vestibular dysfunction, illustrated by circling and shaking of the head. This necessitated that they be raised in a mother-less rescue deck system. Pigs were challenged in a parkour with different hindrance and objects in the test track, towards a food reward at the end.

Figure 5A:
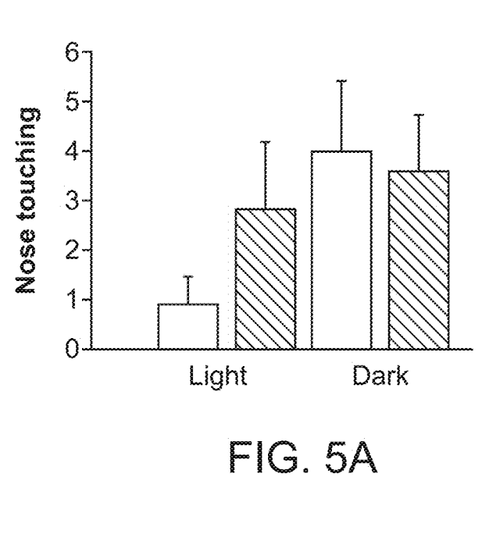
Figure 5B:
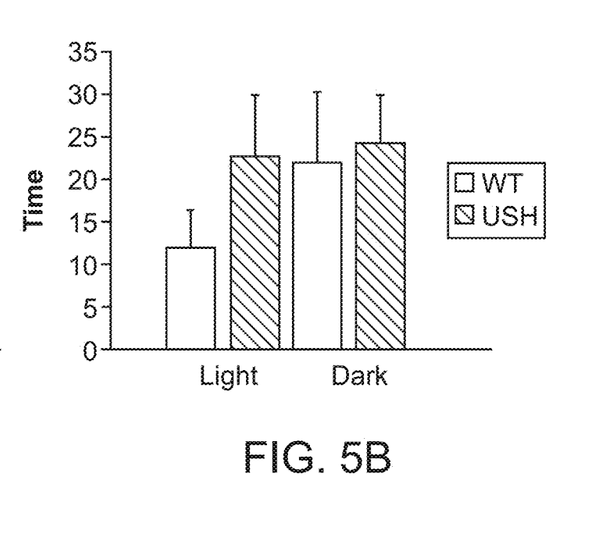

FIGS. 5A and 5B show results of testing for visual acuity in the USH model pigs. Five USH pigs and five wild-type (WT) littermate controls were tested for their ability to cross a parcours containing obstacles under normal light conditions and in darkness. The time for passing the track and number of snout touching have been considered as parameters. Mean values and standard deviations of representative experiments are shown.

The USH1C$^{R31X/R31X}$ pigs (hatched bars) more frequently bumped into hindrance and were much slower than the wild type (WT) control pigs (open bars) in coping with the challenge. These findings indicate visual impairment in the USH1C$^{R31X/R31X}$ pigs.

Inner ear analysis. We tested the inner ear function in Brainstem Auditory Evoked Response (BAER) tests in three week old USH1C$^{R31X/R31X}$ pigs.

Figure 6A:
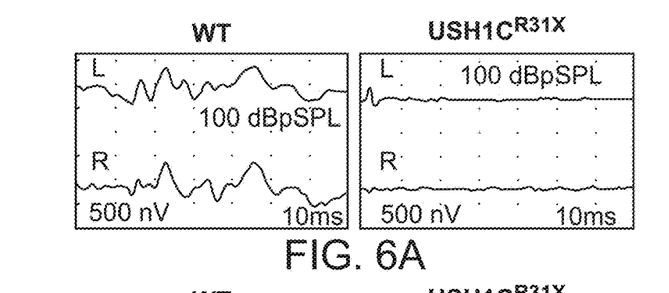
Figure 6B:
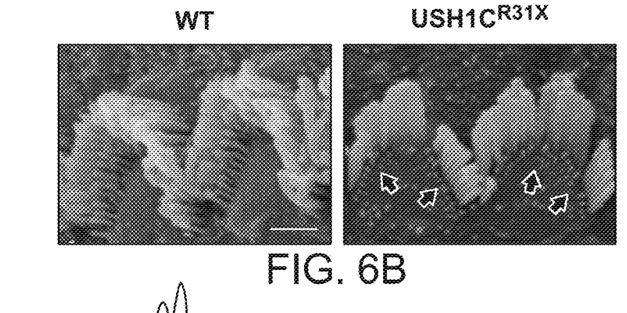
FIG. 6B: Their cochlear outer hair cells lack rows stereocilia (arrows).

FIGS. 6A and 6B show the results. All USH1C$^{R31X/R31X}$ animals were entirely deaf (FIG. 6A). At a structural level, scanning electron microscopy analysis of inner ear hair cells (FIG. 6B) revealed significant morphological differences between WT and USH1C$^{R31X/R31X}$ pigs: Although stereocilia were present in both WT and transgenic pigs, defined rows of stereocilia were absent in cochlear outer hair cells of USH1C$^{R31X/R31X}$ piglets.

Figure 6C:
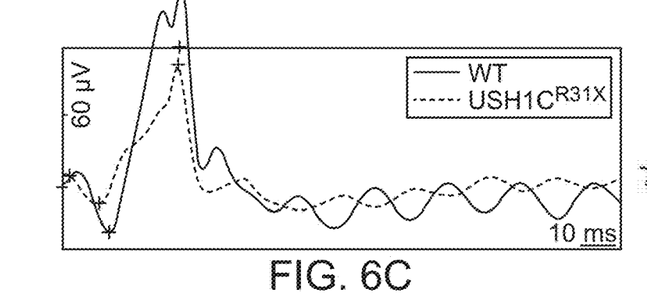
FIG. 6C: Electroretinography (ERG) indicated a definite, but already reduced signal compared to controls.

Analysis of visual function. FIG. 6C shows the results of electroretinography (ERG) recordings. We observed a slightly reduced response in the a- and b-wave amplitude upon light stimulation already in three weeks old USH1C$^{R31X/R31X}$ piglets. The reductions of photopic (cone photoreceptor cells) and scotopic (rod photoreceptors) a- and b-wave amplitudes of the ERGs were manifested in 12 month old USH1C$^{R31X/R31X}$ pigs.

Molecular and morphologic analysis of the retina. We did not detect any expression of the USH1C protein harmonin in the neuronal retina of USH1C$^{R31X/R31X}$ pigs by Western blot analysis using anti-pan-harmonin antibodies (H3).

Figure 6D:
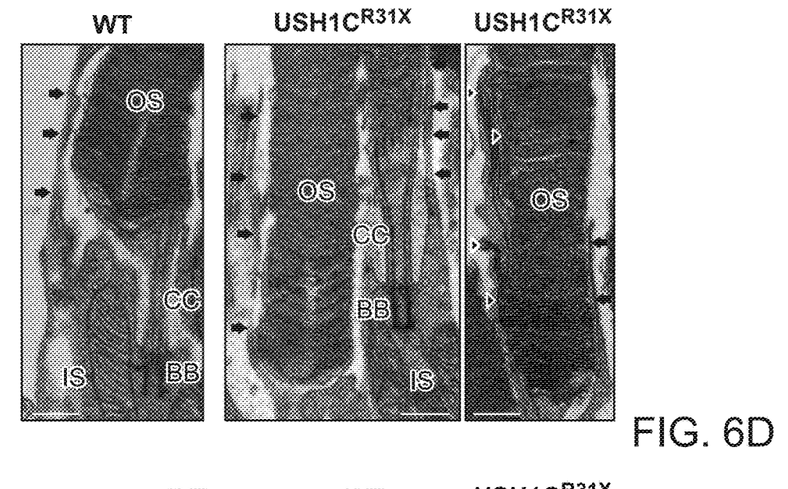
FIG. 6D: Transmission electron microscopy (TEM) of the retina suggested an overall intact architecture of photoreceptor cells, including calyceal processes (black arrows), but the outer segment (OS) intracellularly, the structure of light-sensing shelves was partially affected (white triangles).

FIG. 6D shows an image from transmission electron microscopy (TEM) analysis of retina of three weeks old WT and USH1C$^{R31X/R31X}$ piglets. The overall structure of rods and cones was maintained, including the formation of calyceal processes, but the intracellular architecture in the outer segment was disturbed in the USH1C$^{R31X/R31X}$ homozygotes. This suggests that a structural alteration in the USH1C protein harmonin plays a role in the correct assembly of the disk stacks of light-sensitive membrane shelves. This finding points to a scaffold function of harmonin in the rod outer segment.

An increase of reactive gliosis in Müller glia cells and astrocytes is a reliable biomarker for stress response and retinal degeneration (Iandiev et al. 2006). We analyzed reactive in WT and USH1C$^{R31X/R31X}$ piglet retinas gliosis by immunohistochemistry applying antibodies against glia fibrillary acid protein (GFAP).

Figure 6E:
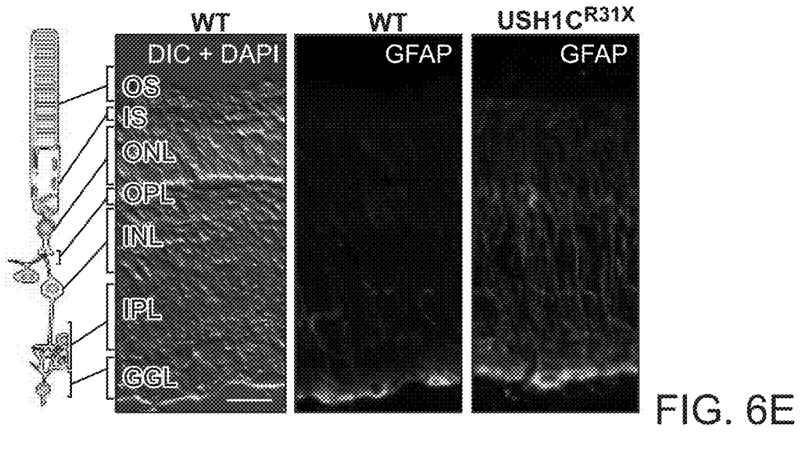
FIG. 6E: Glial fibrillary acidic protein (GFAP), a molecular biomarker for gliosis and retinal degeneration, was upregulated in the retina of USH1C pigs, compared to wild-type (WT) controls.

FIG. 6E shows the results. We found a strong increase in GFAP expression in USH1C$^{R31X/R31X}$ retinas, compared with age-matched wild type (WT) controls. Western blots of retina lysates with anti-GFAP revealed an over 7-fold increase of GFAP expression in USH1C$^{R31X/R31X}$ retinas compared with controls, confirming the immunohistochemical data. The pathomechanisms underlying the retinal degeneration have been initiated even at the early time point of three weeks of age.

Thus, the USH1C$^{R31X/R31X}$ pigs develop a phenotype which resembles not only the inner ear phenotype, pronounced deafness and defects in the vestibular system characteristic of USH, but also the ocular phenotype (prepubertal onset of vison loss) characteristic for human USH type 1.

Use of Homozygous and Heterozygous Animals and Controls

Conventional breeding of pigs carrying the R31X mutation homozygously can be used to produce large cohorts of experimental animals. Alternatively, male and female piglets carrying the R31X nonsense mutations heterozygously as part of a breeding herd can be used to obtain both animals that are homozygous (manifesting signs of USH), and animals without signs (heterozygous mutants and wild type) that can serve as littermate controls.

The user also has the option of using the same technology for creating animals that can serve as vector controls: for example, wherein part or all of the pig USH1C gene is replaced with the corresponding portion of a human USH1C gene that does not bear a mutation. Animals that bear this mutation will produce a fully functional gene product from the modified gene.

Using Animal Models to Develop Therapeutic Agents for Usher Syndrome in Humans

USH1C pigs and other animals produced in accordance with this disclosure can be used for pre-clinical evaluation of a wide range of possible treatment options:

Adeno-associated virus (AAV)-mediated gene therapy. AAV-mediated gene addition of the cDNA of the normal gene is currently the most advanced therapeutic strategy for ocular disorders (discussed in May-Simera et al. 2017). The pig eye with a size close to the human eye allows not only the evaluation of the efficacy of a specific AAV vector but also the application routes, namely injections in the subretinal space, into the vitreus or systemic application.

Translational read-through therapy. USH1C$^{R31X/R31X}$ pigs bear a disease causing nonsense mutation, which generate premature termination codons that cause premature translational termination of the mRNA, and subsequently inhibit normal full-length protein expression. These nonsense mutations are very common in retinal dystrophy genes but also in other monogenic diseases (up to 30%). Translational readthrough (TR) therapy is a gene-based therapeutic approach for genetic diseases caused by nonsense mutations has emerged (Nagel-Wolfrum et al. 2016). TR therapy is based on small molecules, known as TR-inducing drugs (TRIDs), that allow suppression of the nonsense codon resulting in full-length protein synthesis. A pig model according to this disclosure can be used to evaluate TRIDs efficacy, and for testing of delivery routes.

Gene correction via gene editing. By replacing not only the exon 2 but also flanking intronic sequences of the porcine USH1C gene by sequences obtained from a human USH1C patient, gene repair tools (such as CRISPR/Cas9 with a guide RNA having a human-specific sequence) can be tested in our pig model.

Cell or tissue replacement strategies. The USH1C pig and other USH animal models provided in this disclosure allow the user to test any cell- or tissue replacement/transplantation strategies for Retinitis pigmentosa with all advantages of a large animal model for retinal degeneration. These models can also be used to study congenital sensorineural hearing impairment and vestibular defects.

REFERENCES

Iandiev I, Biedermann B, Bringmann A, Reichel MB, Reichenbach A, Pannicke T (2006). Atypical gliosis in Müller cells of the slowly degenerating rds mutant mouse retina. Exp. Eye Res. 82, 449-457.

Klymiuk N, Blutke A, Graf A, Krause S, Burkhardt K, Wuensch A, Krebs S, Kessler B, Zakhartchenko V, Kurome M, et al. (2013). Dystrophin-deficient pigs provide new insights into the hierarchy of physiological derangements of dystrophic muscle. Human Molecular Genetics 22, 4368-4382.

Klymiuk,N, Mundhenk L, Kraehe K, Wuensch A, Plog S, Emrich D, Langenmayer M C, Stehr M, Holzinger A, Kroner C, et al. (2012). Sequential targeting of CFTR by BAC vectors generates a novel pig model of cystic fibrosis. Journal of Molecular Medicine 90, 597-608.

Mathur P and Yang J (2015) Usher syndrome: Hearing loss, retinal degeneration and associated abnormalities. Biochim Biophys Acta 1852(3): 406-420.

May-Simera H, Nagel-Wolfrum K, Wolfrum U (2017) Cilia—the sensory antennae in the eye. Prog Retinal Eye Res. 60:144-180.

Nagel-Wolfrum K, Möller F, Penner I, Baasov T, Wolfrum U (2016) Targeting nonsense mutations in diseases with translational read-through-inducing drugs (TRIDs). BioDrugs 30(2):49-74.

Reiners J, Nagel-Wolfrum K, Jürgens K, Märker T and Wolfrum U (2006) Molecular basis of human Usher syndrome: deciphering the meshes of the Usher protein network provides insights into the pathomechanisms of the Usher disease. Exp Eye Res 83: 97-119.

Reiners J, Reidel B, El-Amraoui A, Boeda B, Huber I, Petit C and Wolfrum U (2003) Differential distribution of harmonin isoforms and their possible role in Usher-1 protein complexes in mammalian photoreceptor cells. Investigative Ophthalmology & Visual Science 44(11): 5006-5015.

Sahly I, Dufour E, Schietroma C, Michel V, Bahloul A, Perfettini I, Pepermans E, Estivalet A, Carette D, Aghaie A, Ebermann I, Lelli A, Iribarne M, Hardelin J P, Weil D, Sahel J A, El-Amraoui A and Petit C (2012) Localization of Usher 1 proteins to the photoreceptor calyceal processes, which are absent from mice. J Cell Biol 199(2): 381-399.

Williams D S (2008) Usher syndrome: animal models, retinal function of Usher proteins, and prospects for gene therapy. Vision Res 48(3): 433-441.

Wolfrum U (2011) Protein networks related to the Usher syndrome gain insights in the molecular basis of the disease. Usher syndrome: pathogenesis, diagnosis and therapy. Ahuja S. USA, Nova Science Publishers Inc.: 51-73.

Wolfrum U and Nagel-Wolfrum K (2018) The usher syndrome, a human ciliopathy. Klin Monbl Augenheilkd. 235(3):273-280

Dameyer J (2012). Children with Usher syndrome: mental and behavioral disorders. Behav Brain Funct. 8(16) doi: 10.1186/1744-9081-8-16.

Hashimoto T, Gibbs D, Lillo C, Azarian S M, Legacki E, Zhang X M, Yang X J, Williams D S. (2007). "Lentiviral gene replacement therapy of retinas in a mouse model for Usher syndrome type 1B". Gene Therapy. 14 (7): 584-594.

Zallocchi M, Binley K, Lad Y, Ellis S, Widdowson P, Iqball S, Scripps V, Kelleher M, Loader J, Miskin J, Peng Y W, Wang W M, Cheung L, Delimont D, Mitrophanous K A, Cosgrove D. EIAV-based retinal gene therapy in the shaker1 mouse model for usher syndrome type 1B: development of UshStat. PLoS One. 2014 Apr. 4; 9(4):e94272.

Blanco-Sánchez B, Clement A, Fierro J Jr, Stednitz S, Phillips J B, Wegner J, Panlilio J M, Peirce J L, Washbourne P, Westerfield M. Grxcr1 Promotes Hair Bundle Development by Destabilizing the Physical Interaction between Harmonin and Sans Usher Syndrome Proteins. Cell Rep. 2018 Oct. 30; 25(5):1281-1291.e4. doi: 10.1016/j.celrep.2018.10.005.

Held N, Smits B M, Gockeln R, Schubert S, Nave H, Northrup E, Cuppen E, Hedrich H J, Wedekind D. A mutation in Myo15 leads to Usher-like symptoms in LEW/Ztm-ci2 rats. PLoS One. 2011 Mar. 29; 6(3): e15669. doi: 10.1371/journal.pone.0015669.

INCORPORATION BY REFERENCE

For all purposes, each and every publication and patent document cited in this disclosure is hereby incorporated herein by reference in its entirety for all purposes to the same extent as if each such publication or document was specifically and individually indicated to be incorporated herein by reference.

Definitions

Reference anywhere in this disclosure or in the claims below to a genetically modified or transgenic animal, tissue, or cell that is "suitable for" or "adapted for" or "configured for" use, "as part of an animal model for Usher syndrome," implies no constraints on the nature or effect of the genetic modification or transgene, or the use of the product. The wording is provided only for the convenience of the reader to suggest possible commercial applicability of the product or method being referred to.

"Genetically modified" means that one or more genes that is normally expressed in the animal referred to has been modified so as to encode a gene product having a different amino acid sequence, a shorter amino acid sequence, or is modified to be non-transcribable. In the context of this invention, the modification becomes part of the genome or the germline.

The term "transgenic" in reference to such animals means that all or part of a gene from another species (or a polynucleotide of artificial construct) has been introduced into the animal, often but not necessarily in place of an endogenous gene.

When genes are referred to in this disclosure according to their USH designation (exemplified in Table 1), the term includes the gene in its endogenous context in the genome, homologs thereof that encode functional proteins, non-functional proteins and fragments, non-expressible genes, and cross-species homologs of any of the above, either in the genome of a cell, or in a gene vector. Such genes are referred to in this disclosure as "USH related" genes, regardless of their species of origin.

Although the genetically modified animals referred to in this disclosure are illustrated in the context of modeling Usher syndrome in humans and the screening of therapeutic agents, these uses are not intended to be limiting. The reader may use the animals and the technology put forth in this disclosure for any suitable purpose, unless otherwise indicated or required.

While the invention has been described with reference to the specific examples and illustrations, changes can be made and equivalents can be substituted to adapt to a particular context or intended use as a matter of routine development and optimization and within the purview of one of ordinary skill in the art, thereby achieving benefits of the invention without departing from the scope of what is claimed and their equivalents.

TABLE 1

Usher Syndrome phenotypes and genes that underlie the pathophysiology

| Type | Gene locus | Gene | Protein | Function | Amino acid Length | UniProt ref. no. |
|---|---|---|---|---|---|---|
| USH1B | 11q13.5 | MYO7A | Myosin VIIA | Motor protein | 2215 | Q13402 |
| USH1C | 11p15.1-p14 | USH1C | Harmonin | PDZ-domain protein: transmembrane anchoring | 552 | Q9Y6N9 |
| USH1D | 10q21-q22 | CDH23 | Cadherin 23 | Cell adhesion | 3354 | Q9H251 |
| USH1E | 21q21 | (unknown) | | | | |
| USH1F | 10q11.2-q21 | PCDH15 | Protocadherin 15 | Cell adhesion | 1955 | Q96QU1 |
| USH1G | 17q24-q25 | USH1G | SANS | Scaffold protein | 461 | Q495M9 |
| USH2A | 1q41 | USH2A | Usherin | PDZ-domain protein: transmembrane anchoring | 5202 | O75445 |
| USH2C | 5q14.3-q21.1 | GPR98 | VLGR1b | G-protein coupled receptor: signal transduction | 6307 | Q8WXG9 |
| USH2D | 9q32-q34 | DFNB31 | Whirlin | PDZ-domain protein: transmembrane anchoring | 907 | Q9P202 |
| USH3A | 3q21-q25 | CLRN1 | Clarin-1 | Synaptic shaping | 232 | P58418 |

TABLE 2

Known mutations of the USH1c gene causing Usher syndrome

| No. | Exon | nucleic acid change | encoded protein change |
|---|---|---|---|
| 1 | 2 | 91C > T | R31X |
| 2 | 3 | 238_239insC | R80fs |
| 3 | 5 | 496 + 1G > A | splice defect |
| 4 | 6 | 497-2delA | splice defect |
| 5 | B | $32G > T | G431V |
| 6 | D | $293C > G | P608R |
| 7 | D | $329G > T | R620L |
| 8 | D | $376C > T | R636C |

Adapted from Cremers PM et al., J Med Genet. 2007 Feb; 44(2): 153-160

The invention claimed is:

1. A genetically modified pig exhibiting phenotypic features of Usher syndrome, whose genome has a substitution in both alleles of the endogenous USH1c pig gene,
wherein each substitution comprises an exogenous nucleic acid that prevents or inhibits expression of a functional USH1c gene product from the respective allele, and
wherein the pig exhibits phenotypic features of Usher syndrome comprising deafness, vestibular dysfunction, and defects in the pig's eyes that manifest as, or will progress to, impaired vision when compared to a wild-type control pig.

2. The genetically modified pig according to claim 1, wherein the exogenous nucleic acid contains a nonsense mutation or a stop codon that terminates transcription of the protein encoded by the USH1c gene.

3. The genetically modified pig according to claim 1, wherein the exogenous nucleic acid comprises a nucleotide sequence of at least part of a human USH1c gene that replaces the part of the endogenous USH1c gene.

4. The genetically modified pig according to claim 1, wherein the substitution in both of the alleles includes part of a human USH1c gene that encodes an R31X mutation that causes Usher syndrome.

5. The genetically modified pig according to claim 1, wherein the exogenous nucleic acid replaces all or part of Exon-2 of the coding region of the endogenous USH1c gene.

6. The genetically modified pig according to claim 1, wherein the exogenous nucleic acid does not contain an exogenous drug resistance gene, but optionally contains at least one lox recombination site.

7. The genetically modified pig according to claim 1, wherein the intracellular architecture of photoreceptor cells in an eye of the pig is abnormal when analyzed by transmission electron microscopy (TEM), compared with an eye in a wild-type control pig.

8. An isolated tissue or cell population removed or isolated from the genetically modified pig of claim 1.

9. A method of producing a genetically modified pig according to claim 1, comprising:
a) introducing an exogenous nucleic acid that prevents or inhibits expression of a functional USH1c gene product from the endogenous USH1c pig gene into the genome of a primary pig cell by way of homologous recombination with a BAC vector that contains the exogenous nucleic acid, thereby producing one or more genetically modified cells;
b) generating a plurality of parental pigs from clonal progeny of the genetically modified cell(s) from step a) by somatic cell nuclear transfer, wherein the presence of the exogenous nucleic acid in the genome of each parental pig prevents or inhibits expression of a functional USH1c gene product from one USH1c allele of the parental pig, and then c) breeding such parental pigs from step b) together to produce an offspring whose genome has a substitution in both alleles of the endogenous USH1c pig gene,
wherein each substitution comprises an exogenous nucleic acid that prevents or inhibits expression of a functional USH1c gene product from the respective allele, and
wherein the pig exhibits phenotypic features of Usher syndrome comprising deafness, vestibular dysfunction, and defects in the pig's eyes that manifest as, or will progress to, impaired vision when compared to a wild-type control pig.

10. The method of claim 9, wherein the homologous recombination of step a) is promoted in the primary pig cell by co-transfecting the primary pig cell with the BAC vector together with plasmids encoding gRNA and Cas9.

11. The method of claim 9, wherein the genetically modified cell of step a) is separated from cells that have not been genetically modified using a drug to which the genetically modified cell is rendered resistant as a result of the presence of the exogenous nucleic acid in the genetically modified cell.

12. The method of claim 9, wherein a plurality of the genetically modified cells of step a) are screened for successful introduction of the exogenous nucleic acid by qPCR-based loss-of-wild-type-allele (LOWA) analysis to select the clonal progeny used for the nuclear transfer.

13. A method for testing a pharmaceutical agent or composition for efficacy in the treatment of Usher syndrome, comprising:
administering the agent or composition in or around an eye of a genetically modified pig according to claim 1, and
determining whether the administering of the agent or composition subsequently prevents or delays the onset or progression of impaired vision in the pig, when compared to an untreated control pig.

14. The method of claim 13, wherein the agent is an adeno-associated virus (AAV) vector containing a gene that produces a functional USH1c gene product when expressed in cells located in or around the eye of the genetically modified pig.

15. The method of claim 13, wherein the composition comprises one or more polynucleotide vectors that are configured for translational read-through (TR) therapy of a genetically modified USH1c gene in the eye of the genetically modified pig.

16. The method of claim 13, wherein the composition comprises one or more polynucleotide vectors that are configured for genetic repair of a genetically modified USH1c gene in the eye of the genetically modified pig.

* * * * *

SEQUENCE LISTING

<160> NUMBER OF SEQ ID NOS: 2

<210> SEQ ID NO 1
<211> LENGTH: 1539
<212> TYPE: DNA
<213> ORGANISM: Porcine

<400> SEQUENCE: 1

```
aggcaagggg gttctgccag gtggaaacca gaaatctgca ttctgtaccc cctgttcagg      60
ccagaaacct caagggctgg gcccagcatg gcctctttgt gttaggccag gcagacttcc     120
tgaaccctga agatatccag agaaagaggc aaagatgctc cagctctcct ctgaggacca     180
atcaggtggg agcttgcagc ttccagcagc agcttctccc tgtgcagcct gaggccctgg     240
accatgttgt tggccctgga tgctggagga cagagggacc caaggacccc tcaagcctcc     300
accctgccct cttactcagt ctgggctgaa gagcgagcta aggatgtagt acataaagat     360
tcatactgag ctgtcccagg gagtgaaatt cggggctctt gacccaccag ctctcctggg     420
actgaggtgc taatgaaaca gctcttgacc ctgaccttgg actcctggcc attgacgtca     480
gcaaaattga ataatgtaa cctgactctc ccctgggt ggaaggggag ctctacaggg        540
acctggggag gggaaggagt ggccagaggg gccaacccag cttagaccag acaggacaa      600
ggaagaattc agtggcaagg ttcttcgggc ggatgggatg tgctatctga gcgagtggcc     660
taaatctttt ctgaaagcgg ttatccggca ctacagccac catcaggtaa gacaatgggc     720
ttctgccgac acgggtggtg ccaccctgga cacaggtgac ataaccatgg aggtgatcag     780
cagcacggct gccgtggggg tgcatcactg tcacacaggg gttcacaggt atgatatgca     840
tatgcatccc tgtgtgcccc tgcatcaccc cacctggggt caggctgatg actacatccg     900
aaagcacaaa ggtgctcctg tggccacact ggcatggtcg gcgcagtctc atgttggaac     960
```

| | | |
|---|---|---|
| cagagggcca gcctggcctc tggcttccct cctcttctca caaccatgag gagacgctgg | 1020 | |
| ggaggttccc cccaccccca cagtggcctc cccttcctg ctgctactgg gggtgctggg | 1080 | |
| cctggagctg taattctgcc cttgggtttt ccaggtggat ttcctgattg aaaatgatgc | 1140 | |
| agaaaaggat tatctctacg atgtgctgcg gatgtaccac cagtaagtgt gctgggtccc | 1200 | |
| actcctgtgg accaccccgg gtacctctgt cctcaggag ccctggggtg tgttgttctg | 1260 | |
| agacaggag acctcccact cccatcctgg gaagctcagg gaggcagatg cctgggaatc | 1320 | |
| aaatggacac gcctttcact ggtttcaaca aatatttaca cagaggtgct gtgcgtggct | 1380 | |
| ctgtgctagg ggctaggagt acgcctgtca gcaagacaga tgagttgctg ccctcaagtt | 1440 | |
| gctcatggtc tgatggggga ggctgtcaga tagtccgaga ggttcaacaa agtttgatgt | 1500 | |
| ctgggatagg accggaaatg ccagctggcc ttagcacca | 1539 | |

```
<210> SEQ ID NO 2
<211> LENGTH: 1524
<212> TYPE: DNA
<213> ORGANISM: Homo sapiens

<400> SEQUENCE: 2
```

| | | |
|---|---|---|
| agggaaggag gtactgtcag atctaggcca gaaatctgca ttctgtaccc cctgctcagg | 60 | |
| ccagaaatcc caagggctgg gcccagcatg tcccctctgt ggtgggacgg acagactgcc | 120 | |
| ccggtcttcc agaacccttg ggatacccac agaaagaggt aacgctgctc tggccctctt | 180 | |
| ctgaggacga gtcagtggag agcatgcagc ttccagctgc agcctctcta tgaagggctg | 240 | |
| aggccctggg ccgggaggct ggaggagaga gggacccagt gaccccccaa gcttccacct | 300 | |
| tgctctgtta cccgttcttg ggctgaagag agacccaaaa atacagtgta gagattcaca | 360 | |
| ctgaggtaac tcagggagtg gaattcaggg cctcccactg ggattgaggt gctaatgaca | 420 | |
| caactcctga acctgacctt agagtgccag ccattgacgt caacaaagtt gaaatgatgt | 480 | |
| aacctgacgc tcccccctgcg gggcttgtgc aggggcctgg ggaggggggaa ggagtggcca | 540 | |
| tgaaactgac tagtggacag aacccagcta aggtcaggac aagacagagt gaaggtcccc | 600 | |
| tggcactgat gttacagaag aattcggtgg taaggggctt ctggagagtg gcatgtgcta | 660 | |
| tctaagcgag tggcccaaat ccttcctgaa agcatttatc cggcactaca gccaccatca | 720 | |
| ggtaagacag tgggcttctt ctggccatgg atgacacagc catggggtg agcagcagca | 780 | |
| ctgccatggc agcgtgtcac tgtcacatgg ggattcacat atgtacctat gtgtgttcat | 840 | |
| ccccgtgtgt gcacatattg cccccacctgg ggacgaaggg tgcctggcca catctggagg | 900 | |
| ggcagcggta ctcctgtggc cacgttgggg tggtctgcat aggtctgatg cattggggtc | 960 | |
| agaggggcag cctggcctgt ggctcctctt ctctcctcac aactccagcc ctgaaaagct | 1020 | |
| gctgggagg cccttgggga tgacctctcc tccctgaggt ctgctatggg tggggtgct | 1080 | |
| gagcctggag ctgtgattct gctattggat tttccaggtg gattttctga ttgaaaatga | 1140 | |
| tgcagagaag gactatctct atgatgtgct gtgaatgtac caccagtaag tgtgctgggt | 1200 | |
| ccagctcttg tgggccactt gggttccttt gtcttcaggg agccctggga tgggttgttc | 1260 | |
| tgagacagag gagctcagag ggtggatgct cacggctcct ggaaatcaaa tggacatacc | 1320 | |
| attcactcat ttcagcaact atttacacaa gtactttgta cttggctttg tactaggggc | 1380 | |
| tgggtatagt tgtgagccag acagattggt ctctgttttc aggttgctca cagtctgatg | 1440 | |

```
gaggaggctg tctagtagcc agatagattc tatagagcat gattgttggg acagaacaag    1500
aaatgccagc tggccacagc cctt                                           1524
```